United States Patent [19]

Kroener et al.

[11] Patent Number: 5,326,909
[45] Date of Patent: Jul. 5, 1994

[54] STABILIZATION OF MONOMERIC N-VINYLFORMAMIDE

[75] Inventors: Michael Kroener, Mannheim; Jacques Dupuis, Ludwigshafen, both of Fed. Rep. of Germany

[73] Assignee: BASF Aktiengesellschaft, Ludwigshafen, Fed. Rep. of Germany

[21] Appl. No.: 65,492

[22] Filed: May 24, 1993

[30] Foreign Application Priority Data

Jun. 3, 1992 [DE] Fed. Rep. of Germany ...... 4218221

[51] Int. Cl.$^5$ .............................. C07C 233/09
[52] U.S. Cl. .......................... 564/4; 564/215
[58] Field of Search ..................... 564/4, 215

[56] References Cited

U.S. PATENT DOCUMENTS 4,814,505  3/1989  Kroener et al. .
5,126,395  6/1992  End et al. ................. 524/801

FOREIGN PATENT DOCUMENTS 0231901  1/1987  European Pat. Off. .
1224304  5/1965  Fed. Rep. of Germany .
2336977  2/1975  Fed. Rep. of Germany .
1289068  12/1986  Japan .

OTHER PUBLICATIONS

Primary Examiner—Mary C. Lee
Assistant Examiner—Jacqueline Haley
Attorney, Agent, or Firm—Oblon, Spivak, McClelland, Maier & Neustadt

[57] ABSTRACT

A method of stabilizing N-vinylformamide, which may contain customary polymerization inhibitors, against polymerization during storage or transport, comprises adding to the N-vinylformamide monomers of the general formula

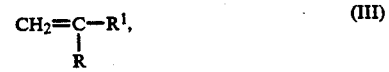

where
R+H, $CH_3$

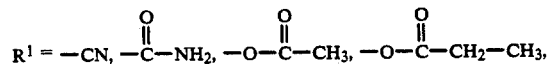

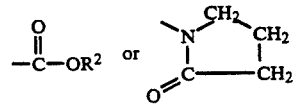

$R^2 + C_1-C_4$-alkyl, as stabilizer in amounts of from 1 to 99 % by weight, based on the mixture.

3 Claims, No Drawings

STABILIZATION OF MONOMERIC N-VINYLFORMAMIDE

The present invention relates to a method for stabilizing N-vinylformamide, which may contain customary polymerization inhibitors, against polymerization during transport or storage.

N-vinylformamide can be prepared for example by the process of DE-C-1 224 304 by eliminating hydrogen cyanide from formyl alanine nitrile of the formula

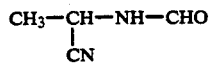
(I)

in the presence of a solid catalyst under reduced pressure at preferably 300–500° C. According to the process disclosed in DE-A 2 336 977, the N-vinylformamide is obtained from N-α-methoxyethylformamide of the formula

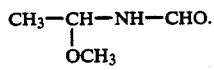
(II)

by elimination of methanol. In either case the N-vinylformamide obtained as pyrolysis product is thermally very sensitive and will even polymerize in the course of the distillation unless pressures below about 1 mbar are employed. According to the process disclosed in EP-B-0 231 901, the purification of N-vinylformamide is effected by a fractional distillation under pressure of from 0.5 to 30 mbar in the presence of formamide. More specifically, the distillation is controlled in such a way that the distillate obtained comprises N-vinylformamide containing from 0.1 to 15% by weight of formamide.

The polymerization tendency of N-vinylformamide can be contained to some extent by the use of customary stabilizers for monoethylenically unsaturated monomers, e.g. phenols or aromatic amines, only at room temperature or below. At higher temperatures, for example at 60° C., and especially in the presence of air, N-vinylformamide will initially polymerize slowly but later —if heat removal is inadequate-explosively, even in the presence of customary stabilizers.

It is an object of the present invention to provide a method for stabilizing bulk amounts of N-vinylformamide to effectively raise the polymerization onset temperature of N-vinylformamide.

We have found that this object is achieved by a method of stabilizing N-vinylformamide, which may contain customary polymerization inhibitors, against polymerization during storage or transport, which comprises adding to the N-vinylformamide monomers of the general formula

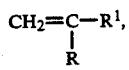
(III)

where
R+H, CH$_3$

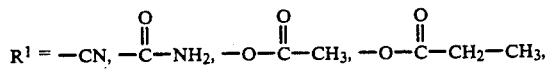

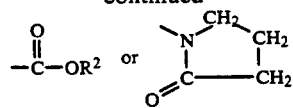

$R^2$+C$_1$-C$_4$-alkyl, as stabilizer. The use of monomers of the formula III as stabilizers for the storage and transport of N-vinylformamide in amounts of from 1 to 99% by weight, based on vinylformamide, was unforseeable, since the monomers used as stabilizers are, like the N-vinylformamide, not stable and tend to polymerize in the presence of impurities or at elevated temperatures.

The invention succeeds in stabilizing N-vinylformamide against premature polymerization during storage or transport. The N-vinylformamide may contain customary polymerization inhibitors such as nitrosophenol, N,N'-disec-butyl-p-phenylenediamine, hydroquinone monomethyl ether and phenothiazine in the customary amounts of from 5 to 1000 ppm. However, these polymerization inhibitors do not ensure adequate stabilization of N-vinylformamide against premature polymerization during storage or transport. The invention provides as stabilizers monomers of the formula

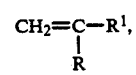
(III)

where
R+H, CH$_3$

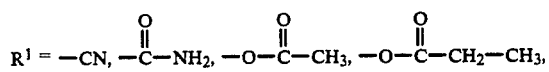

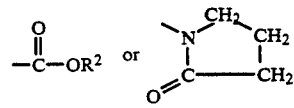

$R^2$+C$_1$-C$_4$-alkyl.

Compounds of the abovementioned formula are acrylonitrile, methacrylonitrile, acrylamide, methacrylamide, vinyl acetate, vinyl propionate and esters of acrylic acid and methacrylic acid derived from alcohols of from 1 to 4 carbon atoms, e.g. methyl acrylate, ethyl acrylate, n-propyl acrylate, isopropyl acrylate, n-butyl acrylate, isobutyl acrylate, tert-butyl acrylate, methyl methacrylate, ethyl methacrylate, isopropyl methacrylate, n-butyl methacrylate, isobutyl methacrylate and tert-butyl methacrylate. The preferred stabilizers are acrylonitrile, acrylamide, vinyl acetate and vinyl propionate. The monomers of the formula III are used in amounts of from 1 to 99, preferably from 5 to 95, % by weight, based on the mixture. The addition of these monomers to N-vinylformamide raises the onset temperature of the mixture. By onset temperature is meant the lowest ambient temperature at which a noticeable exothermic reaction starts in the sample. An increase in the onset temperature of a monomer or monomer mixture means that the monomer(s) in question can be safely stored and transported at correspondingly higher temperatures.

To stabilize N-vinylformamide it is advantageous to select those monomers of the formula III which are to be copolymerized with N-vinylformamide, e.g. vinyl acetate, vinyl propionate or acrylonitrile or else mixtures of monomers, such as mixtures of N-vinylformamide, vinyl acetate and acrylamide or mixtures of N-vinylformamide, acrylonitrile and acrylamide. The pH of the N-vinylformamide stabilized with at least one monomer of the formula III is within the range from 5.0 to 8.0, preferably from 6.0 to 7.0. This pH is determined by taking a sample of the mixture, mixing it with distilled water in a ratio of 1:1 and measuring the pH with a glass electrode at 20° C.

EXAMPLES

The onset temperatures reported in the table were determined by differential thermal analysis (DTA). Of each of the monomers specified in the table 30 mg were heated in a closed V4A steel crucible with a constant temperature ramp of 2.0 K per minute. In each case the temperature difference between the in-test sample and an inert reference sample (air) was measured as a function of the oven temperature as a measure of the heat flow. The sample pH, measured as described above, was in each case 6.2. The results are summarized in the table.

TABLE

| Operative example | Comparative example | Investigated composition of N-vinylformamide [% by weight] | Stabilizing monomer | [% by weight] | Onset temperature [°C.] |
| --- | --- | --- | --- | --- | --- |
|   | 1 | 100 | — |   | 80 |
| 1 | — | 67 | vinyl acetate | 33 | 130 |
| 2 | — | 50 | vinyl acetate | 50 | 130 |
| 3 | — | 50 | N-vinylpyrrolidone | 50 | 100 |
| 4 | — | 50 | acrylonitrile | 50 | 110 |

As is evident from the table, by adding monomers to N-vinylformamide it is possible to raise the onset temperature by up to 50° C. compared with a nonstabilized N-vinylformamide.

We claim:

1. A method of stabilizing N-vinylformamide, which may contain customary polymerization inhibitors, against polymerization during storage or transport, which comprises adding to the N-vinylformamide monomers of the general formula $$CH_2=\underset{R}{C}-R^1, \quad (III)$$

where
R + H, CH$_3$

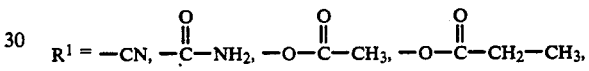

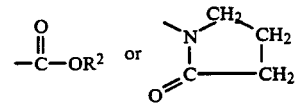

R$^2$ + C$_1$-C$_4$-alkyl,
as stabilizer.

2. A method as claimed in claim 1 wherein the stabilizer used is acrylonitrile, acrylamide, vinyl acetate or vinyl propionate.

3. A method as claimed in claim 1 or 2 wherein the stabilizer is used in an amount of from 1 to 99% by weight, based on the mixture.

* * * * *